(12) United States Patent
Zhu et al.

(10) Patent No.: US 12,131,893 B1
(45) Date of Patent: Oct. 29, 2024

(54) METHOD OF IDENTIFYING TOBACCO CARBONYL COMPONENTS USING NON-TARGETED MASS SPECTROMETRY

(71) Applicant: CHINA TOBACCO YUNNAN INDUSTRIAL CO., LTD., Kunming (CN)

(72) Inventors: Ruizhi Zhu, Kunming (CN); Xiaoxi Si, Kunming (CN); Yanqun Xu, Kunming (CN); Zhihua Liu, Kunming (CN); Ji Yang, Kunming (CN); Wei Jiang, Kunming (CN); Chunbo Liu, Kunming (CN); Fengmei Zhang, Kunming (CN); Zhenjie Li, Kunming (CN); Shiyun Tang, Kunming (CN)

(73) Assignee: CHINA TOBACCO YUNNAN INDUSTRIAL CO., LTD., Kunming (CN)

( * ) Notice: Subject to any disclaimer, the term of this patent is extended or adjusted under 35 U.S.C. 154(b) by 0 days.

(21) Appl. No.: 18/497,574

(22) Filed: Oct. 30, 2023

Related U.S. Application Data (63) Continuation of application No. PCT/CN2023/102744, filed on Jun. 27, 2023.

(30) Foreign Application Priority Data

Jun. 25, 2023 (CN) .......................... 202310751411.3

(51) Int. Cl.
*G01N 30/86* (2006.01)
*G01N 1/10* (2006.01)
(Continued)

(52) U.S. Cl.
CPC ............ *H01J 49/0036* (2013.01); *G01N 1/10* (2013.01); *G01N 30/8631* (2013.01);
(Continued)

(58) Field of Classification Search
CPC ...... H01J 49/0036; H01J 49/425; G01N 1/10; G01N 30/8631; G01N 30/8679;
(Continued)

(56) References Cited

U.S. PATENT DOCUMENTS 11,604,176 B2    3/2023   Han et al.
2020/0355656 A1  11/2020  Han et al.

FOREIGN PATENT DOCUMENTS

CN    104950064 A    9/2015
CN    106018635 A    10/2016
(Continued)

OTHER PUBLICATIONS

Miller. UHPLC Separation with MS Analysis for Eight Carbonyl Compounds in Mainstream Tobacco Smoke. 2010 (Year: 2010).*
(Continued)

*Primary Examiner* — Rebecca M Fritchman
(74) *Attorney, Agent, or Firm* — Andrew D. Fortney; Central California IP Group, P.C.

(57) ABSTRACT

A method of identifying tobacco carbonyl components using non-targeted mass spectrometry is disclosed, which includes the following steps: (1) preparing a tobacco sample extract; (2) derivatizing (part of) the sample/extract with 2,4-dinitrophenylhydrazine (DNPH); (3) derivatizing (another part of) the sample/extract with DNPH-$d_3$; (4) mixing the derivatized tobacco samples; (5) preparing blank samples; (6) performing ultra performance liquid chromatography (UPLC) and ion trap (Orbitrap) high resolution mass spectrometry (HRMS) on the (derivatized) tobacco samples; (7) processing the LC-MS data; (8) filtering the mass spectrometric characteristic data to retain final chromatographic peaks; and (9) structurally annotating or identifying the retained final chromatographic peaks to obtain the tobacco carbonyl components. The method quickly removes noise or
(Continued)

interfering components in the original data set by multiple filtering of the mass spectrometry characteristic data, and enables obtaining composition information of aldehyde and ketone chemical components in cigarettes.

20 Claims, 2 Drawing Sheets

(51) Int. Cl.
*G16C 20/20* (2019.01)
*H01J 49/00* (2006.01)
*H01J 49/42* (2006.01)
*G01N 30/02* (2006.01)
*G16C 20/30* (2019.01)

(52) U.S. Cl.
CPC ........ *G01N 30/8679* (2013.01); *H01J 49/425* (2013.01); *G01N 2001/1006* (2013.01); *G01N 2030/027* (2013.01); *G16C 20/20* (2019.02); *G16C 20/30* (2019.02)

(58) Field of Classification Search
CPC ..... G01N 2001/1006; G01N 2030/027; G16C 20/20; G16C 20/30
See application file for complete search history.

(56) References Cited

FOREIGN PATENT DOCUMENTS

| CN | 107966518 A | 4/2018 |
|---|---|---|
| CN | 110646535 A | 1/2020 |
| CN | 110806456 A | 2/2020 |
| CN | 112433015 A | 3/2021 |
| CN | 112684033 A | 4/2021 |
| CN | 112684034 A | 4/2021 |
| CN | 113156028 A | 7/2021 |
| WO | 20220262132 A1 | 12/2022 |

OTHER PUBLICATIONS

Andra. UHPLC Separation with MS Analysis for Eight Carbonyl Compounds in Mainstream Tobacco Smoke. 2017 (Year: 2017).*
CN105021733A (English translation) 2015. (Year: 2015).*
Tan. Application of multiple statistical tests to enhance mass spectrometry-based biomarker discovery. 2009 (Year: 2009).*
WANG in CN 108037201 (English translation).2020 (Year: 2020).*
Deng in CN 106018635 (English translation).2016 (Year: 2016).*
DATOR in A High Resolution/Accurate Mass (HRAM) Data-Dependent MS3 Neutral Loss Screening, Classification and Relative Quantitation Methodology for Carbonyl Compounds in Saliva. 2017 (Year: 2017).*
Written Opinion dated Oct. 23, 2023; International Application No. PCT/CN2023/102744; International Filing Date Jun. 27, 2023; 3 pages; China National Intellectual Property Administration (ISA/CN), Beijing, China.
International Search Report dated Oct. 23, 2023; International Application No. PCT/CN2023/102744; International Filing Date Jun. 27, 2023; 3 pages; China National Intellectual Property Administration (ISA/CN), Beijing, China.
Chao et al., "Analysis of 8 Carbonyl Compound in Smokeless Tobacco Products and Cigarette Filler by UPLC-IE Method," Food Industry, vol. 38, Issue 3, Mar. 20, 2017, pp. 256-261; China Academic Journal Electronic Publishing House, www.cnki.net.

* cited by examiner

METHOD OF IDENTIFYING TOBACCO CARBONYL COMPONENTS USING NON-TARGETED MASS SPECTROMETRY

CROSS-REFERENCE TO RELATED APPLICATIONS

This application is a continuation of International Pat. Appl. No. PCT/CN2023/102744, filed on Jun. 27, 2023, which claims the benefit of Chinese Pat. Appl. No. 202310751411.3, filed on Jun. 25, 2023, both of which are incorporated herein by reference as if fully set forth herein.

TECHNICAL FIELD

The disclosure belongs to the field of tobacco technology, and specifically relates to a method of identifying tobacco carbonyl components using non-targeted mass spectrometry. By filtering the mass spectrometry characteristic data and performing structural identification on the retained chromatographic peaks, tobacco carbonyl components can be obtained.

BACKGROUND

Aldehydes and ketones are important carbonyl compounds commonly found in biological organisms and the human living environment. Fatty aldehydes or ketones with low molecular weight (carbon chain length<10) can react with biomolecules such as DNA, proteins, and enzymes, and are highly cytotoxic and genotoxic; formaldehyde, acetaldehyde, and crotonaldehyde have been classified by the International Agency for Research on Cancer (IARC) as Category 1, Category 2B and Category 3 human carcinogens, respectively. Acrolein is included in the "List of Hazardous Air Pollutants" by the US Environmental Protection Agency (US EPA); formaldehyde, acetaldehyde, acetone, acrolein, propionaldehyde, crotonaldehyde, 2-butanone and butyraldehyde, etc. are listed on the Hoffmann list.

Aldehydes and ketones are the most numerous aroma components in tobacco. Currently, more than 500 aldehydes and ketones have been identified in smoke. In view of the important impact of aldehydes and ketones on flavor and safety in cigarette systems, it is very important to conduct a comprehensive qualitative and quantitative analysis of them. Researchers have carried out a lot of work on the qualitative and quantitative analysis of aldehyde and ketone components in different systems based on gas chromatography-mass spectrometry (GC-MS) or liquid chromatography-mass spectrometry (LC-MS). Among them, LC-MS technology combines the strong separation capabilities of LC with the high specificity and sensitivity of MS, and has become one of the most prominent technologies in the field of qualitative and quantitative analysis of small molecule compounds. Depending on the purpose of the research, targeted or non-targeted data collection methods can be used to analyze the target substance. The targeted LC-MS method mainly targets known target components and provides accurate content information through quantitative analysis using external standard methods and other methods. However, targeted methods usually only focus on a small number of target components for which chemical standards are available. However, there may be many potentially important components in complex sample systems that cannot be targeted for analysis due to the lack of suitable chemical standards.

Compared with targeted analysis, non-targeted LC-MS technology focuses on the analysis and detection of all possible targets in the sample system. Represented by ion trap (Orbitrap) mass spectrometry or time-of-flight (TOF) mass spectrometry, etc., high resolution mass spectrometry (HRMS) has been widely used in non-targeted identification and detection of unknown components due to its extremely high resolution and mass accuracy. LC-HRMS can provide rich data information such as precise molecular weight, isotope distribution and multi-level mass spectrometry. Currently, LC-HRMS has been widely used in the fields of metabolomics, environmental analysis and food safety analysis, by obtaining a large number of known and unknown components. The chromatography-mass spectrometry signal provides the possibility to comprehensively understand the chemical composition of the test sample.

Small molecule aldehydes and ketones have the characteristics of diverse structures, large differences in polarity, high volatility, low ionization efficiency, and wide concentration ranges. Their highly sensitive non-targeted analysis using LC-MS still faces many difficulties. Chemical derivatization (chemical labeling) treatment is an important method to improve the LC behavior of the target and increase the sensitivity and specificity of MS detection. So far, researchers have developed a series of detection methods for aldehydes and ketones with chemical derivatization reactions combined with LC-QqQ-MS or LC-HRMS, using p-nitrophenylhydrazine, 2,4-dinitrophenylhydrazine, Girard reagent T, and ammonium acetate-phenanthrenequinone as derivatization reagents. It can be seen that the use of derivatization reaction combined with LC-HRMS detection can significantly improve the performance of LC-MS technology in detecting small molecule aldehydes and ketones.

However, the data sets generated by LC-HRMS experiments are very large and complex. How to process these complex raw data and quickly identify and determine target components in complex matrices has always been a very difficult task. First of all, the complex raw data contains thousands of mass spectral features, which contain a particularly large amount of redundant chromatographic-mass spectrometric information. Even in a blank sample that does not contain the target substance, it is possible to detect thousands of chromatograms with good peak shapes. In addition, the concentration distribution of compounds in complex samples is wide, and the mass spectral signals of low-abundance targets may be overwhelmed by background noise ions or signals from matrix interfering ions due to their low intensity. Therefore, it is difficult to intuitively extract chromatography-mass spectrometry information of low-abundance target components from raw data, increasing the difficulty of their qualitative and quantitative analysis.

Data cleaning and mass spectrometry information filtering can help us efficiently identify and specify target components from complex LC-HRMS data sets, especially those trace target components with very low abundance. Based on the chromatographic behavior and mass spectrometry characteristics of the target class of compounds, different data cleaning methods and mass spectrometry information filtering strategies can be designed to achieve efficient filtering of interfering ions in the original data and targeted extraction of target components. For example, metabolomic analysis uses the coefficient of variation of chromatographic peaks (mass spectral features) in quality control samples to evaluate stability, which can eliminate a large number of detected interfering chromatographic peaks. In drug metabolism analysis, by setting a specific mass loss window, the chromatography-mass spectrometry signals of many interfering components can be filtered out, allowing the exposure of similar drug metabolites with specific structures. In natural product analysis, neutral loss filtering and diagnostic fragment ion filtering can be used to quickly identify some chemical components with similar chemical structures. However, many currently proposed LC-MS filtering methods still set filters based on a single dimension of chromatographic or mass spectrometric information. Therefore, there are still shortcomings, such as low information filtering efficiency and too many false positive results. In particular, there are currently no mass spectrometric filtering methods that incorporate chemical derivatization labeling information. Therefore, it is expected to improve the filtering specificity and accuracy of LC-MS raw data by comprehensively utilizing statistical analysis, chromatographic behavior, mass spectrometry characteristics and other information of the target component to design a multi-dimensional chromatography-mass spectrometry data filtering method.

Overall, aldehydes and ketones are important chemical components in the tobacco system, and their non-target recognition and identification are of great significance. However, there is still a lack of an efficient method to achieve this purpose. There are the following difficulties in identifying and specifying aldehydes and ketones in complex sample systems: 1. Aldehydes and ketones have small molecular weights and low ionization efficiency, making it difficult to directly detect them with high sensitivity using LC-MS technology; 2. The distribution range of similar components of aldehydes and ketones is wide, and the LC-MS technique used must have a wide dynamic range in analysis and detection to capably distinguish among different components; 3. The original LC-MS data contains a large amount of interfering component chromatography-mass spectrometry information, which can drown out the target component information, especially low-abundance chromatography-mass spectrometry signals of target components, and can make the recognition and identification of aldehydes and ketones very difficult.

SUMMARY

The present disclosure is proposed for this purpose.

The present method and system use derivatization reactions to chemically label potential aldehyde and ketone compounds, establish and optimize an LC-HRMS method to perform highly sensitive detection of aldehyde and ketone derivatization products, and employ multi-dimensional data filtering technology based on statistical characteristics, chromatographic behavior, mass spectrometry characteristics and isotope labeling information, thereby enabling efficient recognition and identification of aldehyde and ketone components in complex LC-MS data sets through automated processing.

A method for identifying tobacco carbonyl components, including those of relatively low-molecular weight aldehydes and ketones, may comprise:
(1) soaking a tobacco product with water, then adding a certain amount of acetonitrile for oscillation extraction (e.g., extraction by shaking) to obtain a tobacco extract;
(2) taking a certain amount of the tobacco extract and adding a certain amount of 2,4-dinitrophenylhydrazine (DNPH) to it for derivatization to obtain a first tobacco sample (CCs-DNPH);
(3) using DNPH-$d_3$ instead of DNPH and repeating Step (2) to obtain a second tobacco sample (CCs-DNPH-$d_3$) with an isotope-label;
(4) taking the first tobacco sample and the second tobacco sample in a ratio of 1:1, mixing them thoroughly, and filtering them through a filter membrane to obtain a third tobacco sample;
(5) preparing a blank sample following Steps (1) and (2) except for soaking a tobacco product in water;
(6) performing ultra performance liquid chromatography (UPLC) and ion trap (Orbitrap) high resolution mass spectrometry (HRMS) on the first tobacco sample, the second tobacco sample, the third tobacco sample and the blank sample to obtain original LC-MS data;
(7) performing peak detection, peak alignment and peak grouping on the original LC-MS data to obtain original mass spectral feature data for a coexistence of target components and interfering components, including m/z value, retention time and peak intensity;
(8) performing multiple filtering on the original mass spectral feature data to obtain final retained chromatographic peaks; and
(9) annotating or structurally identifying the final retained chromatographic peaks to obtain (identities of) the tobacco carbonyl components.

Preferably, the conditions for UPLC and Orbitrap HRMS analysis include:

Performing UPLC-HRMS with an instrument platform comprising a Dionex U3000 UHPLC system and a Q-Exactive mass spectrometer connected in series;

UPLC conditions including: a Syncronis C18 column (2.1 mm×100 mm, 1.7 μm); a column temperature: 40° C.; an injection volume: 1 μL; a mobile phase A: 0.1% formic acid aqueous solution; a mobile phase B: acetonitrile; a gradient elution program: 0~1 min 95% B, 1~3 min 95%~60% B, 3~10 min 60%~10% B, 10~18 min 10% B, 18~19 min 10%~95% B, 19~20 min 95% B; and a flow rate: 0.2 mL/min;

Mass spectrometry conditions including: a spray voltage of 3.7 kV, a sheath gas flow rate of 35 L/min, an auxiliary gas flow rate of 10 L/min, and a DL transfer tube temperature of 350° C.; and Collecting data in a negative ion mode of Full MS-DDA, wherein a mass-to-charge ratio scanning range of primary mass spectrometry is 100-1200 m/z, with a resolution of 70,000; a mass-to-charge ratio scanning resolution of secondary mass spectrometry is 35,000, and a high-energy collision-induced dissociation voltage is 30 eV.

Preferably, performing multiple filtering on the mass spectrometry characteristic data includes: filtering the mass spectrometry characteristic data based on statistical characteristics, filtering the mass spectrometry characteristic data based on mass loss, filtering the mass spectrometry characteristic data of paired chromatographic peaks based on one or more markers of a derivatization reaction, and filtering of mass spectrometry characteristic data based on secondary mass spectrometry and/or multiple ion mass spectrometry characteristics to obtain the final retained chromatographic peaks;

Preferably, the step of filtering mass spectrum characteristic data based on statistical characteristics includes:

Calculating the coefficient of variation (CV) and fold change (FC) according to the formulas CV=IntSQC/IntMQC$_1$×100%, where IntSQC represents the standard deviation of the peak intensity of a specific chromatographic peak in the first tobacco sample, and IntMQC$_1$ represents the average peak intensity, and FC=IntMQC$_2$/IntMBK, where IntMQC$_2$ represents the average peak intensity of specific chromatographic peaks in the first tobacco sample, and IntMBK represents the average peak intensity of specific chromatographic peaks in the blank sample; and Retaining the corresponding chromatographic peak when CV≤30% and FC≥1.5.

Preferably, the step of filtering mass spectrometry characteristic data based on mass loss includes:

Calculating (e.g., an m/z value) according to the formula MD=|MZ−ceiling (MZ)|, where MZ represents an accurate mass of a precursor ion of the specific chromatographic peak in the first tobacco sample (that is, the m/z value), and ceiling (MZ) is the ceiling or rounded-up integer number of the accurate mass (e.g., of the precursor ion of the specific chromatographic peak in the first tobacco sample; that is, the nominal mass); and Retaining the corresponding chromatographic peak when 0.02≤MD≤0.3 and m/z>209.

Preferably, the step of filtering the mass spectrometry characteristic data of paired chromatographic peaks based on marker(s) of the derivatization reaction includes: detecting a pair of chromatographic peaks in the third tobacco sample at the same retention time, then retaining the pair of chromatographic peaks when |MZ−MZd$_3$|=3.0186, ||IntP1−IntP2|/max(P1, P2)<30%, and |RT1−RT2|<2, wherein MZ and MZd$_3$ respectively represent the accurate mass of the precursor ion of a non-isotopically labeled tobacco carbonyl component and a corresponding isotope d$_3$-labeled derivatization product (that is, the m/z value, e.g., of the precursor ion of the isotope d$_3$-labeled derivatization product), IntP1 and IntP2 represent the peak areas of the first and second chromatographic peaks, respectively, and RT1 and RT2 represent the retention times of the first and second chromatographic peaks, respectively.

Preferably, the filtering method based on the secondary mass spectrometry multiple ion mass spectrum characteristics includes: retaining the corresponding chromatographic peaks when the secondary mass spectrum of the first tobacco sample produces fragment ions of m/z 76.018, m/z 120.008, m/z 122.024, m/z 135.019 and m/z 181.012.

Preferably, the structural annotation or identification of the final retained chromatographic peaks includes standard product matching, database searching, or cracking pattern analysis.

Preferably, Step (7) includes peak detection peak alignment and peak grouping processing, Step (8) includes multiple filtering of mass spectrometry characteristic data, and Step (9) includes structural annotation or identification (e.g., of the precursor ion[s] and/or other tobacco carbonyl components) on the final retained chromatographic peaks, which can be automated in the system and/or using one or more software packages.

Beneficial effects of the present disclosure:

1. The method of the present disclosure quickly eliminates noise and/or interfering components from the original mass spectrometry information/data set by multiple filtering of the mass spectrometry data, and efficiently identifies mass spectral characteristics and chromatographic peaks that truly belong to aldehyde and ketone chemical components from complex, non-targeted data sets. Based on the extracted chromatographic peaks and mass spectrometry characteristics of chemical components belonging to aldehydes and ketones, their chemical structures are annotated using methods such as standard product matching, database retrieval, and cracking rule analysis to obtain the chemistry of aldehydes and ketones in cigarettes or food samples.

2. The present disclosure has developed a data processing package (MSFiltering package) for peak detection, peak alignment and peak grouping processing of original LC-MS data to obtain mass spectral characteristics for coexisting target components and interfering components. Based on statistical characteristics, quality multi-dimensional data filtering methods for depletion, isotope labeling and secondary mass spectrometry multiple ion information, as well as structural identification of the final retained chromatographic peaks, etc., efficient identification and identification of aldehyde and ketone components in complex LC-MS data sets can be achieved through automated processing.

DETAILED DESCRIPTION

The present invention will be further described in detail below through specific embodiments, but the scope of the present invention is not limited to the following examples. Without departing from the concept(s) of the present invention, various substitutions and changes made based on common and/or conventional technical knowledge in the art should be included in the scope of the present invention.

Example: Method of identifying tobacco carbonyl components using non-targeted mass spectrometry, comprising the following steps:
(1) soaking a tobacco product with water, then adding a certain amount of acetonitrile for oscillation extraction (e.g., extraction by shaking) to obtain a tobacco extract;
(2) taking a certain amount of the tobacco extract and adding a certain amount of 2,4-dinitrophenylhydrazine (DNPH) to it for derivatization to obtain a first tobacco sample (CCs-DNPH);
(3) repeating Step (2) using DNPH-$d_3$ to obtain a second tobacco sample (CCs-DNPH-$d_3$) with an isotope label;
(4) mixing the first tobacco sample and the second tobacco sample in a ratio of 1:1 thoroughly, and filtering them through a filter membrane to obtain a third tobacco sample;
(5) preparing a blank sample (e.g., containing no tobacco product[s]) according to Steps (1) and (2);
(6) performing ultra performance liquid chromatography (UPLC) and ion trap (Orbitrap) high-resolution mass spectrometry (HRMS) on the first tobacco sample, the second tobacco sample, the third tobacco sample and the blank sample to obtain original LC-MS data;
(7) performing peak detection, peak alignment and peak grouping on the original LC-MS data to obtain original mass spectral feature data, including m/z value, retention time and peak intensity, of coexisting target components and interfering components;
(8) performing multiple filtering on the original mass spectral feature data obtained in Step (7) to obtain final retained chromatographic peaks;
(9) annotating or identifying structurally the tobacco carbonyl components from the final retained chromatographic peaks.

Detailed steps include:
Step 1: Cut the raw tobacco material into pieces of about 0.5 cm×0.5 cm in area; take 1.0 g of the raw tobacco material (accurate to 0.1 mg), place it in a 100 mL stoppered Erlenmeyer flask, add 5 mL of water, and wait until the sample is completely infiltrated with water. Then add 30 mL of acetonitrile accurately, shake it on an oscillator at 150 r/min for 30 minutes to and extract tobacco components from the raw tobacco material, and obtain a sample extract solution.

Step 2: Accurately transfer 1.0 mL of the tobacco sample extract solution into a 10 mL volumetric flask, add 4 mL of DNPH, dilute to volume (10 ml) with acetonitrile, shake well, and place at room temperature for 30 minutes to derivatize tobacco components in the raw tobacco material and prepare a first tobacco sample (CCs-DNPH).

Step 3: Repeat Step 2 using DNPH-$d_3$ instead of DNPH to prepare an isotope-labeled second tobacco sample (CCs-DNPH-$d_3$).

Step 4: In a ratio of 1:1, take 1 mL each of the first tobacco sample (CCs-DNPH) and the second tobacco sample (CCs-DNPH-$d_3$), mix thoroughly, and filter through a 0.22 μm organic phase filter to obtain a third tobacco sample.

Step 5: Prepare a blank sample according to the above Steps 1-4, except that there is no water infiltration step of tobacco raw materials (i.e., the raw tobacco material is omitted in Step 1).

Step 6: Perform UPLC and Orbitrap HRMS on the first tobacco sample, the second tobacco sample, the third tobacco sample and the blank sample to obtain original LC-MS data.

The conditions for UPLC-Orbitrap HRMS analysis include:

UPLC-HRMS is performed with an instrument platform comprising a Dionex U3000 UHPLC system and a Q-Exactive mass spectrometer, connected in series.

UPLC conditions include a Syncronis C18 column (2.1 mm×100 mm, 1.7 μm), a column temperature of 40° C., an injection volume of 1 μL, a first mobile phase (mobile phase A) comprising a 0.1% aqueous solution of formic acid, a second mobile phase (mobile phase B) comprising acetonitrile, and a gradient elution program as follows: minutes 0~1: 95% mobile phase B, minutes 1~3: 95%~60% mobile phase B, minutes 3~10: 60%~10% mobile phase B, minutes 10~18: 10% mobile phase B, minutes 18~19: 10%~95% mobile phase B, and minutes 19~20: 95% mobile phase B, all at a flow rate of 0.2 mL/min;

Mass spectrometry conditions include a spray voltage of 3.7 kV, a sheath gas flow rate of 35 L/min, an auxiliary gas flow rate of 10 L/min, and a DL transfer tube temperature of 350° C. Data collection was performed in the negative ion mode of Full MS-DDA. The mass-to-charge ratio scanning range of the primary mass spectrometer was set to 100-1200 m/z, with a resolution of 70,000. The mass-to-charge ratio scanning resolution of the secondary mass spectrometry was 35,000. The high-energy collision-induced dissociation voltage is 30 eV.

Step 7: Performing peak detection, peak alignment and peak grouping on the original LC-MS data to obtain original mass spectral feature data, which may include coexisting target components and interfering components. The data includes m/z values, retention times and peak intensities.

Step 8: Filtering the original mass spectral feature data obtained in Step (7) multiple times (e.g., according to 2, 3 or more different filtering criteria, such as statistical characteristics, mass loss, paired chromatographic peaks based on derivatization reaction markers, secondary mass spectrometry characteristics, and/or multiple ion mass spectrometry characteristics) to obtain final retained chromatographic peaks.

Filtering mass spectrum feature data based on statistical features may include:

Calculating the coefficient of variation (CV) and fold change (FC) according to the formulas CV=IntSQC/IntMQC$_1$×100%, where IntSQC represents the standard deviation of the peak intensity of a specific chromatographic peak in the first tobacco sample, and IntMQC$_1$ represents the average peak intensity (e.g., of specific chromatographic peaks in the first tobacco sample), and FC=IntMQC$_2$/IntMBK, wherein IntMQC$_2$ represents the average peak intensity of specific chromatographic peaks in the first tobacco sample, and IntMBK represents the average peak intensity of specific chromatographic peaks in the blank sample. In these calculations, IntMQC$_1$ may equal IntMQC$_2$.

If CV≤30% and FC≥1.5, the corresponding chromatographic peak(s) are retained.

Filtering mass spectrometry characteristic data based on mass loss may include:

Calculating a mass deviation (MD) according to the formula MD=|MZ−ceiling (MZ)|, wherein MZ represents the accurate mass of the precursor ion of or corresponding to a specific chromatographic peak (e.g., corresponding to the precursor ion) in the first tobacco sample (that is, the m/z value), and ceiling (MZ) is the ceiling or rounded-up number of the accurate mass (that is, the nominal mass of the precursor ion corresponding to the specific chromatographic peak).

If 0.02≤MD≤0.3, and m/z (MZ)>209, the corresponding chromatographic peak is retained.

Filtering the mass spectrometry characteristic data based on pairs of chromatographic peaks including the derivatization reaction markers includes: detecting a pair of chromatographic peaks in the third tobacco sample at the same retention time, and retaining the corresponding chromatographic peaks when $|MZ-MZd_3|=3.0186$, $|IntP1-IntP2|/\max(P1, P2)<30\%$, and $|RT1-RT2|<2$. MZ and MZd3 respectively represent the accurate mass and/or the m/z value of the precursor ions of (i) a particular non-isotopically labeled tobacco carbonyl component and (ii) the corresponding isotope $d_3$-labeled derivatization product, IntP1 and IntP2 represent the peak areas of the first and second chromatographic peaks, respectively, and RT1 and RT2 respectively represent the retention times of the first and second chromatographic peaks of the pair of chromatographic peaks.

Filtering based on the secondary mass spectrometry multiple ion mass spectrum characteristics includes retaining the corresponding chromatographic peaks when the secondary mass spectrum of the first tobacco sample produces fragment ions of m/z 76.018, m/z 120.008, m/z 122.024, m/z 135.019 and m/z 181.012.

Step 9: Structurally annotating or identifying the finally retained chromatographic peaks may include standard product matching, database search, and/or cracking pattern analysis.

Steps 7, 8 and 9 above may be performed automatically using one or more software packages. Such software packages may be commercially available (e.g., from Thermo Fisher Scientific Inc., Waltham, Massachusetts, USA).

The present disclosure develops a data processing package (MSFiltering package) based on the R language, which is used to perform peak detection, peak alignment and peak grouping processing on the original LC-MS data to obtain mass spectral characteristics for coexisting target components and interfering components. Based on statistical characteristics, multi-dimensional data filtering methods for mass loss or mass defects, isotope labeling and secondary mass spectrometry multiple ion information, as well as structural annotation or identification of the final retained chromatographic peaks, etc., can achieve efficient identification of aldehyde and ketone components in complex LC-MS data sets through automated processing identification and authentication.

Figure 4:
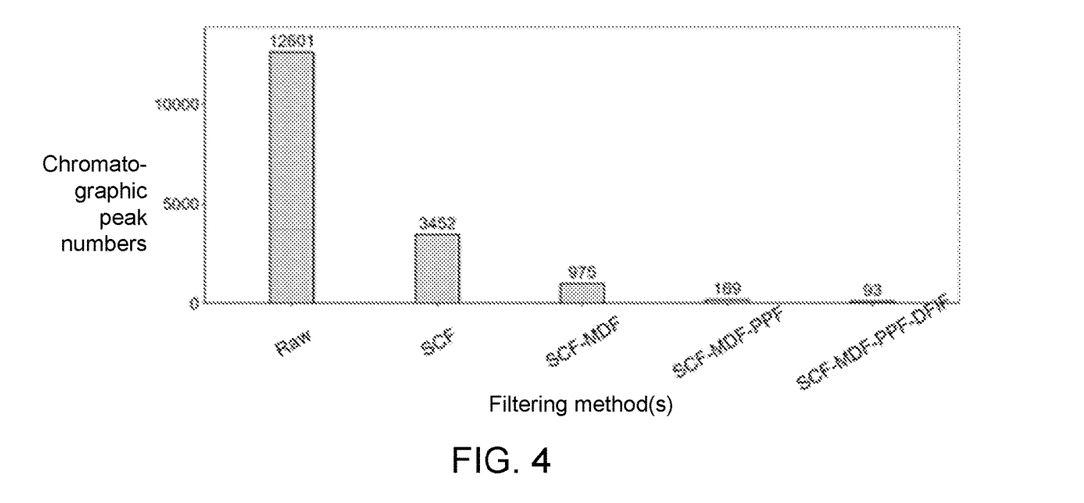
FIG. 4 is a graph of the number of characteristic peaks of a tobacco sample taken in accordance with an embodiment of the invention, the number of characteristic peaks after filtering the mass spectrometry characteristic data based on statistical characteristics, the number of characteristic peaks after filtering the mass spectrometry characteristic data based on mass loss, and the number of characteristic peaks after filtering mass spectral characteristic data of paired chromatographic peaks labeled based on derivatization reaction markers, and the number of characteristic peaks after filtering based on the multiple ion mass spectrometry characteristics of secondary mass spectrometry.

Using an embodiment of the invention, FIG. 4 shows the number of raw characteristic peaks of a tobacco sample, the number of characteristic peaks after filtering the mass spectrometry characteristic data based on statistical characteristics (SCF), the number of characteristic peaks after filtering the mass spectrometry characteristic data based on mass loss or mass defects (MDF), the number of characteristic peaks after filtering based on the paired chromatographic peaks including derivatization reaction markers (PPF), and the number of characteristic peaks after filtering based on the multiple ion mass spectrometry characteristics of secondary mass spectrometry (DFIF).

As can be seen from FIG. 4, the number of original characteristic peaks of the tobacco sample was 12601. After mass spectrometry characteristic data filtering (SCF) based on statistical characteristics, the number of retained chromatographic peaks was reduced to 3452 (a decrease of 72.6%); based on mass loss after mass spectral characteristic data filtering (MDF), the number of retained chromatographic peaks continued to decrease to 975 (a decrease of 92.3%); after mass spectral characteristic data filtering (PPF) based on pairs of chromatographic peaks including derivatization reaction markers, the number of retained chromatographic peaks continued to decrease to 169 (a decrease of 98.6%); and after secondary mass spectrometry multiple ion mass spectrometry characteristic filtering (DFIF), the number of retained chromatographic peaks was reduced to 93 (a decrease of 99.3%). By evaluating their EIC quality, molecular formula prediction, primary and secondary mass spectrometry quality, 70 chromatographic peaks were finally retained, based on standard comparison and literature or database searching, and these were analyzed by comparing retention times, MS and MS/MS data. The retained chromatographic peaks were used for structural identification. For unknowns that did not have standards or known mass spectrum information, Frontier 7.0 (Thermo Fisher Scientific) was used to analyze the mass spectrum fragmentation patterns and annotate their chemical structures. The identification results are shown in Table 1, including molecular formula, secondary mass spectrum, annotation results and other information. Among them, 40 chromatographic peaks had obtained structural annotations, and the corresponding chemical structures of another 20 chromatographic peaks were further inferred. The annotated chromatographic peaks include hydrazones (i.e., the DNPH derivatization reaction products) of aldehydes or ketones such as formaldehyde, acetaldehyde, 2,3-butanedione, pyruvaldehyde, hydroxyacetone, furfural, 5-hydroxymethylfurfural, benzaldehyde, and salicylaldehyde.

The results show that there is a large amount of redundant information in the original LC-MS data. The method of the present invention can efficiently eliminate interference information through multiple mass spectrometry filtering and quickly identify potential aldehyde and ketone chemical components from non-targeted data sets.

Figure 1:
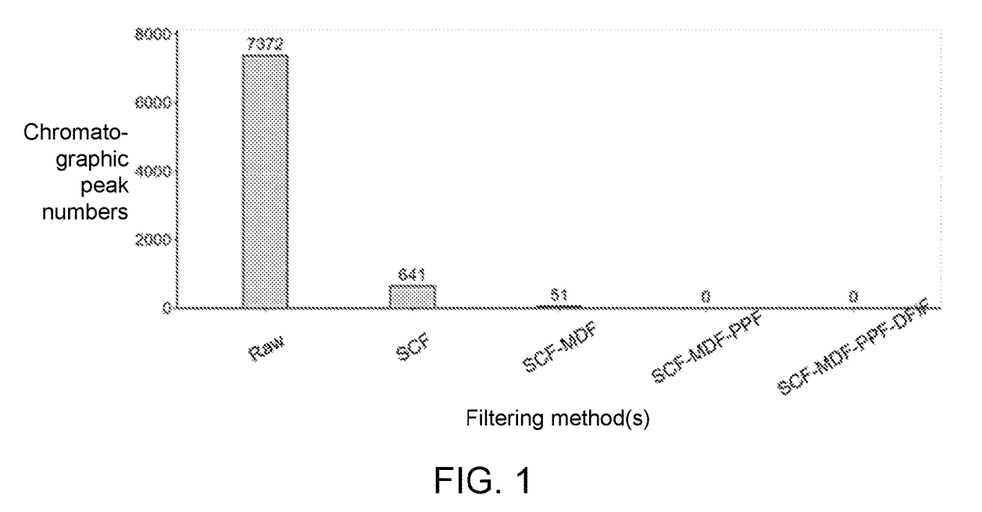
FIG. 1 is a graph showing the number of characteristic peaks of the blank sample in Comparative Example 1 below, the number of characteristic peaks after filtering mass spectrometry characteristic data based on statistical characteristics, the number of characteristic peaks after filtering mass spectrometry characteristic data based on mass loss, the number of characteristic peaks after filtering mass spectral characteristic data of paired chromatographic peaks labeled in a derivatization reaction, and the number of characteristic peaks after filtering based on multiple ion mass spectrometry characteristics of secondary mass spectrometry.

Comparative Example 1: The same multiple filtering was performed on the mass spectrometry characteristic data of the blank sample prepared in the above Example, and the results are shown in FIG. 1. As can be seen from FIG. 1, the number of original (raw) characteristic peaks of the blank sample was 7372. After filtering the mass spectrometric feature data based on statistical characteristics (SCF), the number of retained chromatographic peaks was reduced to 641; after filtering the mass spectrometric feature data based on mass loss (MDF), the number of retained chromatographic peaks was reduced to 51; after filtering the mass spectrometric feature data based on pairs of chromatographic peaks including derivatization reaction markers (PPF), the number of retained chromatographic peaks was reduced to 0.

Figure 2:
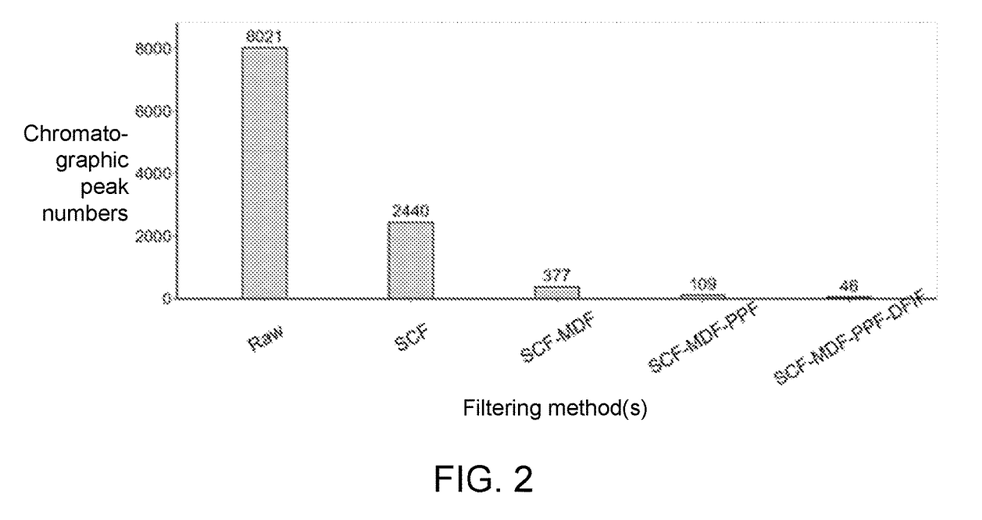
FIG. 2 is a graph showing the number of characteristic peaks of the mixed sample of Comparative Example 2 below, the number of characteristic peaks after filtering mass spectrometry characteristic data based on statistical characteristics, the number of characteristic peaks after filtering mass spectrometry characteristic data based on mass loss, the number of characteristic peaks after filtering mass spectral characteristic data of paired chromatographic peaks labeled based on derivatization reaction, and the number of characteristic peaks after filtering based on multiple ion mass spectrometry characteristics of secondary mass spectrometry.

Comparative Example 2: The same multiple filtering was performed on the mass spectral characteristic data of the mixed standard sample prepared according to the above Example. The preparation steps of mixed standard samples are the same as those described above. 24 known aldehydes and 24 known ketones were added to the mixed standard sample. The 24 aldehydes are: formaldehyde, acetaldehyde, acrolein, glyoxal, n-propionaldehyde, crotonaldehyde, malondialdehyde, n-butyraldehyde, valeraldehyde, furfural, glutaraldehyde, hexanal, benzaldehyde, 5-methylfurfural, n-heptaldehyde, phenylacetaldehyde, salicylaldehyde, 1-octanal, trans-cinnamaldehyde, 2,5-dimethylbenzaldehyde, p-methoxy-benzaldehyde, 2,4-nonadienal, 2,4-nonadienal, and decanal; and the 24 ketones are: acetone, cyclopentanone, 2,3-butanedione, 3-methyl-2-cyclopentenone, cyclohexanone, 2-methyltetra-hydrofuran-3-one, 3-hepten-2-one, 4-heptanone, acetophenone, 2,3-heptanedione, isophorone, alpha-ionone, hydroxyacetone (acetol), 2-pentanone, acetoin, 2,3-pentanedione, methylisobutylketone, 2,3-hexanedione, 2-heptanone, acetoxy-2-propanone, 6-methyl-3,5-benzene-2-one, 6-methyl-6-benzene-2-one, 4-methylacetophenone, and 5-nonanone. each known aldehyde and ketone was added in a concentration of 0.1 mg/mL. The results of multiple filtering of the mass spectral characteristic data of the mixed standard sample are shown in FIG. 2. As can be seen from FIG. 2, the number of original (raw) characteristic peaks of the mixed standard sample is 8021. After filtering the mass spectral characteristic data based on statistical characteristics, the number of the retained chromatographic peaks was reduced to 2440; after filtering the mass spectrometric feature data based on mass loss, the number of retained chromatographic peaks was reduced to 377; after filtering the mass spectrometric feature data based on pairs of chromatographic peaks including derivatization reaction markers, the number of retained chromatographic peaks was reduced to 109; after filtering the mass spectrometry characteristic data based on the multiple ion mass spectrometry characteristics of secondary mass spectrometry, the number of retained chromatographic peaks was reduced to 46. By observing the filtered reconstructed TIC, many interfering mass spectrometry signals were eliminated, and the chromatographic peaks of the target have been significantly exposed, while they were not revealed in the original TIC. This sharp reduction in the number of interfering mass spectrometry features very well narrowed the scope of identification of aldehydes and ketones.

Figure 3:
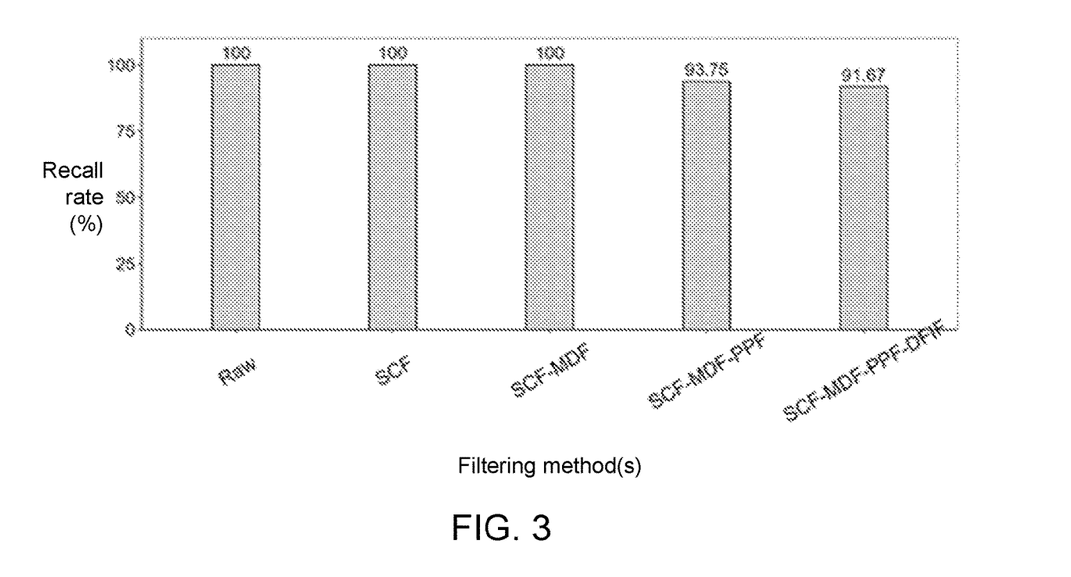
FIG. 3 is a graph showing the recall rate of a mixed standard sample in Comparative Example 2 below, the recall rate after filtering the mass spectrometry feature data based on statistical features, the recall rate after filtering the mass spectrometry feature data based on mass loss, the recall rate after filtering the mass spectra of paired chromatographic peaks based on derivatization reaction markers, and the recall rate after filtering based on multiple ion mass spectrometry features characteristics of secondary mass spectrometry.

The recall rates obtained by filtering the mass spectral features of mixed standard samples using different filtering methods are shown in FIG. 3. As can be seen from FIG. 3, the recall rates of the original data set, statistical feature filtering, and statistical features combined with quality loss filtering are all 100%. The recall rate of statistical features combined with mass loss, paired chromatographic peaks and multiple product ion filtering is greater than 91%, indicating that the added standards can be effectively identified, proving the effectiveness of the multiple filtering method.

TABLE 1

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| 1 | 6.27 | 329.0740 | 150.0525 | C5H10O5 | 78.96 (62.9), 96.97 (55.6), 122.02 (18.4), 141.09 (13.7), 152.02 (14), 182.02 (86.2), 209.08 (100), 210.08 (10.2), 225.07 (13.5) | unknown |
| 2 | 6.72 | 327.0588 | 148.0369 | C5H8O5 | 59.01 (30.6), 76.02 (11.4), 78.96 (52.1), 96.97 (36.9), 122.02 (28.9), 130.09 (12.9), 137.03 (12.7), 152.02 (28.4), 177.02 (20.2), 182.02 (100), 183.01 (15.1) | unknown |
| 3 | 6.89 | 269.0537 | 90.0315 | C3H6O3 | 59.01 (20.7), 65.01 (21.6), 66 (15.9), 78.96 (100), 96.97 (29.7), 106.04 (11.5), 121.03 (11.1), 122.02 (92.1), 125.04 (13.1), 152.02 (24.4), 182.02 (61.9), 185.04 (16.4) | Glyceraldehyde |
| 4 | 6.89 | 295.0683 | 116.0471 | C5H8O3 | 61.99 (26), 78.96 (100), 79.96 (17.1), 96.96 (40.1), 96.97 (37.2), 108.02 (12.7), 122.02 (34.3), 137.03 (69.4), 138.02 (29.2), 158.92 (11.4), 167.03 (34.7), 182.02 (38.9), 230.86 (15.4) | unknown |
| 5 | 7.03 | 280.0692 | 101.0475 | C4H7NO2 | 76.02 (11.3), 78.96 (48.6), 96.97 (19.7), 108.02 (11.8), 122.02 (93), 137.03 (100), 138.02 (18.6), 152.02 (55.3), 167.03 (25) | Acetoacetamide |
| 6 | 7.17 | 323.0646 | 144.0420 | C6H8O4 | 69.03 (10.6), 78.96 (100), 83.02 (10.5), 96.96 (14.2), 96.97 (67.1), 122.02 (12.7), 125.01 (15.1), 182.02 (61.1), 242.86 (21.3), 323.17 (11.5) | Triacetic acid |
| 7 | 7.17 | 341.0753 | 162.0525 | C6H10O5 | 78.96 (20.6), 96.97 (16.3), 122.02 (14.2), 152.02 (12.6), 182.02 (100), 340.2 (11.7) | unknown |
| 8 | 7.24 | 280.0691 | 101.0475 | C4H7NO2 | 76.02 (13.2), 78.96 (58.9), 96.97 (22.6), 108.02 (12.2), 122.02 (100), 137.03 (99.6), 138.02 (18.9), 152.02 (58.7), 167.03 (24) | unknown |
| 9 | 7.34 | 269.0537 | 90.0315 | C3H6O3 | 65.01 (16.5), 66 (11.3), 78.96 (80.7), 96.97 (21.7), 122.02 (100), 152.02 (23.8), 182.02 (62.9), 185.04 (12.8) | unknown |

TABLE 1-continued

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| 10 | 7.58 | 311.0637 | 132.0420 | C5H8O4 | 122.02 (15.7), 182.02 (61.9), 183.01 (100), 311.17 (82.3), 312.17 (14.6) | unknown |
| 11 | 7.65 | 341.0742 | 162.0525 | C6H10O5 | 78.96 (14), 96.97 (18.2), 122.02 (11.3), 182.02 (100) | unknown |
| 12 | 7.66 | 325.0427 | 146.0213 | C5H6O5 | 122.02 (10.5), 182.02 (78.6), 183.01 (81.9), 325.19 (100), 326.19 (19) | unknown |
| 13 | 8.08 | 323.0646 | 144.0420 | C6H8O4 | 78.96 (41.6), 96.97 (25.1), 122.02 (25.5), 152.02 (11.2), 182.02 (100) | unknown |
| 14 | 8.19 | 281.0532 | 102.0315 | C4H6O3 | 78.96 (34.1), 96.97 (13.1), 122.02 (56.6), 152.02 (17.6), 182.02 (100) | Acetoacetic acid |
| 15 | 8.24 | 267.0379 | 88.0159 | C3H4O3 | 65.01 (19.3), 66 (20.5), 76.02 (30.5), 78.96 (60.2), 96.96 (22.5), 96.97 (12.6), 120.01 (36.5), 122.02 (40.7), 135.02 (54.9), 151.01 (36.5), 164.01 (33.4), 169.02 (21.9), 181.01 (100), 182.02 (16.5) | Glucosereductone isomer |
| 16 | 8.27 | 253.0583 | 74.0366 | C3H6O2 | 108.02 (12.3), 122.02 (100), 138.02 (12.3), 152.02 (14.9), 182.02 (10.8) | Hydroxyacetone |
| 17 | 8.27 | 253.0583 | 74.0366 | C3H6O2 | 108.02 (12.3), 122.02 (100), 138.02 (12.3), 152.02 (14.9), 182.02 (10.8) | Hydroxyacetone isomers |
| 18 | 8.32 | 359.0636 | 180.0420 | C9H8O4 | 78.96 (11), 120.01 (10.1), 122.02 (12.8), 135.02 (11.2), 151.01 (10.7), 181.01 (100), 182.02 (34.3) | unknown |
| 19 | 8.48 | 249.0633 | 70.0417 | C4H6O | 65.01 (23.2), 66 (10.3), 78.96 (100), 79.96 (46.2), 80.97 (25.5), 81.04 (25.2), 96.97 (13.7), 105.02 (13), 132.04 (10.9), 184 (69.6), 184.5 (18.9) | Crotonaldehyde isomers |
| 20 | 8.69 | 295.0687 | 116.0471 | C5H8O3 | 78.96 (16), 81.04 (13.3), 122.02 (100), 138.02 (14.8), 152.02 (32.2), 153.03 (11.1), 182.02 (45.5) | Cyclotene |
| 21 | 8.81 | 305.0534 | 126.0315 | C6H6O3 | 50 (11.5), 65.01 (17.5), 66 (20.6), 76.02 (51.9), 78.96 (47.8), 96.97 (28.7), 105.02 (16.6), 120.01 (26.7), 122.02 (38.2), 125.01 (11.6), 135.02 (24.2), 151.01 (12.8), 152.02 (10.6), 163.03 (31.9), 164.01 (12.9), 181.01 (42.7), 182.02 (100), 212.05 (19) | 5-Hydroxymethylfurfural |
| 22 | 8.90 | 267.0736 | 88.0522 | C4H8O2 | 78.96 (12.7), 108.02 (14.7), 122.02 (100), 138.02 (20.6), 152.02 (31.5), 181.01 (10.4), 182.02 (40.7) | acetogamy |
| 23 | 9.01 | 537.0978 | 178.0474 | C6H10O6 | 182.02 (100) | Gluconolactone |
| 24 | 9.08 | 317.0529 | 138.0315 | C7H6O3 | 78.96 (12.5), 134.02 (20.8), 182.02 (100), 196.89 (21.3) | Gentisate aldehyde |
| 25 | 9.11 | 309.0850 | 130.0627 | C6H10O3 | 78.96 (30.2), 95.06 (12.9), 96.96 (65), 96.97 (11.5), 116.93 (10.1), 122.02 (100), 138.02 (20.7), 152.02 (48.3), 153.03 (14.3), 182.02 (44.5), 309.17 (12.9) | unknown |
| 26 | 9.18 | 209.0312 | 30.0105 | CH2O | 65.01 (61.5), 66 (49), 76.02 (100), 78.96 (99.9), 89.01 (24.7), 90.01 (12.2), 91.02 (16.9), 99.92 (21.1), 105.02 (25.7), 120.01 (31.7), 122.02 (15.8), 135.02 (29.3) 121.03 (91.5), 138.02 | formaldehyde |
| 27 | 9.28 | 593.2477 | 234.1970 | H26N8O6 | (19.3), 165.02 (14.5), 209.05 (100), 210.05 (10.1) | unknown |

TABLE 1-continued

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| 28 | 9.46 | 267.0379 | 88.0159 | C3H4O3 | 78.96 (14.1), 122.02 (36.6), 152.02 (12.4), 182.02 (100) | Glucosereductone |
| 29 | 9.46 | 305.0534 | 126.0315 | C6H6O3 | 65.01 (34.1), 67.02 (11), 69.03 (12.5), 76.02 (71), 78.96 (79.1), 79.96 (17.1), 83.02 (20.7), 96.97 (42.3), 97.03 (15.4), 99.92 (22), 105.02 (19.4), 106.04 (23.3), 116.93 (24.2), 120.01 (36.4), 122.02 (51.4), 125.01 (20), 130.04 (10.4), 135.02 (34.5), 151.01 (13.2), 152.02 (15), 163.03 (46.9), 164.01 (21), 169.02 (12.1), 181.01 (57.1), 182.02 (100), 196.89 (12.8), 212.05 (26.9), 240.04 (14.1) | unknown |
| 30 | 9.48 | 359.0636 | 102.0678 | C9H8O4 | 182.02 (100) | unknown |
| 31 | 9.48 | 281.0893 | 180.0420 | C5H10O2 | 50 (10.7), 59.01 (29.9), 65.01 (45.3), 66 (30.1), 66.01 (12.7), 76.02 (45.6), 78.96 (72.7), 81.04 (12.2), 82.04 (16.3), 83.02 (15.1), 87.04 (16.5), 89.01 (10.3), 91.03 (16), 96.96 (14.4), 96.97 (22.6), 99.92 (22), 105.02 (15), 106.04 (41.7), 116.93 (16.2), 120.01 (30.5), 120.06 (13.7), 122.02 (100), 130.04 (13), 132.06 (13.7), 135.02 (23.8), 151.01 (14.5), 152.02 (71.2), 153.03 (22.8), 157.05 (12.4), 163.03 (32.6), 164.01 (13.4), 171.07 (12.4), 181.01 (76.2) | 3-Acetyl-1-propanol |
| 32 | 9.52 | 323.0636 | 144.0420 | C6H8O4 | 78.96 (18.9), 81.03 (13.5), 122.02 (22), 152.02 (10.3), 182.02 (100) | unknown |
| 33 | 9.58 | 267.0737 | 88.0522 | C4H8O2 | 78.96 (41.8), 96.96 (13.2), 108.02 (10.9), 122.02 (100), 138.02 (15), 152.02 (31.4), 182.02 (87.6) | Acetoin isomers |
| 34 | 9.95 | 223.0472 | 44.0261 | C2H4O | 50 (23.2), 58.03 (11.9), 59.01 (10.8), 65.01 (36.4), 66 (29.9), 76.02 (65.9), 78.96 (70.8), 89.01 (16.4), 90.01 (10.7), 99.92 (17), 105.02 (12.6), 108.02 (19.4), 120.01 (27.7), 122.02 (100), 130.04 (11.2), 135.02 (20.1), 138.02 (12.8), 151.04 (21.4), 155.04 (11.3) | Acetaldehyde |
| 35 | 9.98 | 301.0586 | 122.0366 | C7H6O2 | 78.96 (35), 118.03 (30.1), 122.02 (12.5), 182.02 (100) | Salicylaldehyde |
| 36 | 9.99 | 339.0587 | 160.0369 | C6H8O5 | 116.93 (12.6), 182.02 (31.3), 183.01 (54.8), 339.2 (100), 340.2 (21.1) | unknown |
| 37 | 10.15 | 265.0583 | 86.0366 | C4H6O2 | 78.96 (17.2), 96.96 (100) | 2,3-butanedione |
| 38 | 10.17 | 331.0686 | 152.0471 | C8H8O3 | 133.02 (13.9), 182.02 (100) | Vanillin |
| 39 | 10.48 | 381.1063 | 202.0837 | C9H14O5 | 78.96 (32.5), 85.03 (12.1), 96.96 (47.3), 96.97 (25.1), 99.92 (11.4), 116.93 (26.3), 122.02 (24.6), 127.04 (15.3), 138.02 (15.1), 152.02 (46.5), 163.01 (18.3), 167.01 (19.8), 181.01 (100), 181.99 (11.2), 182.02 (30.1), 204.04 (11.5), 205.02 (13.7), 243.03 (28.2), 381.23 (30.5) | unknown |
| 40 | 10.53 | 449.2051 | 270.1840 | C16H22N4 | 122.02 (14.7), 138.02 (14.4), 152.02 (100), 153.03 | unknown |

TABLE 1-continued

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| | | | | | (30.7), 179.02 (34), 182.02 (10.2) | |
| 41 | 10.59 | 291.0738 | 112.0522 | C6H8O2 | 65.01 (20.7), 78.96 (51.4), 96.97 (24.9), 99.92 (16.5), 106.04 (26.7), 116.93 (16.1), 122.02 (99.1), 135.02 (10.6), 152.02 (33), 153.03 (11.6), 181.01 (13.7), 182.02 (100), 196.89 (13.8) | Cyclotene |
| 42 | 10.61 | 261.0637 | 82.0417 | C5H6O | 65.01 (25.3), 66 (15.3), 76.02 (11.2), 78.96 (100), 96.97 (16.4), 99.92 (29.7), 106.04 (11.9), 120.01 (10.4), 122.02 (10.7), 135.02 (23.8), 164.01 (12.2), 179.89 (14.6), 181.01 (25.7) | 2-Methylfuran |
| 43 | 10.62 | 275.0429 | 96.0210 | C5H4O2 | 50 (21.4), 65.01 (11.6), 66 (33.7), 67.02 (26.2), 76.02 (100), 78.96 (52.8), 89.01 (10.8), 95.01 (10.5), 96.97 (43.1), 99.92 (10.4), 105.02 (27), 120.01 (47.3), 122.02 (65.6), 125.01 (20.3), 135.02 (71.9), 146.02 (10.4), 151.01 (32.1), 152.02 (12), 163.02 (30.9), 164.01 (29.5), 169.02 (10.3), 180 (10.5), 181.01 (59.7), 182.02 (77.8) | Furfural |
| 44 | 10.71 | 237.0632 | 58.0417 | C3H6O | 50 (12.4), 65.01 (10.6), 66 (14.5), 76.02 (39.5), 78.96 (11.4), 108.02 (11.9), 116.93 (16.3), 120.01 (13.8), 122.02 (100), 135.02 (13.6), 152.02 (13.3) | acetone |
| 45 | 10.84 | 351.1313 | 172.1095 | C9H16O3 | 76.02 (18.3), 78.96 (27.9), 96.96 (13), 96.97 (29.1), 116.93 (13.1), 122.02 (65.4), 136.03 (12), 138.02 (20.8), 152.02 (100), 153.03 (15.7), 163.03 (38.5), 181.01 (10.4), 182.02 (15.6) | Butyl levulinate |
| 46 | 10.89 | 345.0842 | 164.0834 | C9H10O3 | 182.02 (100), 185.04 (26.4) | Homovanillin |
| 47 | 10.89 | 343.1052 | 166.0627 | C10H12O2 | 181.01 (11.8), 182.02 (100) | 4-(4-Hydroxyphenyl)-2-butanone |
| 48 | 10.90 | 237.0632 | 59.0495 | C3H8O | (11.4), 108.02 (11.9), 116.93 (16.3), 120.01 (13.8), 122.02 (100), 135.02 (13.6), 152.02 (13.3) | Propionaldehyde |
| 49 | 10.97 | 485.0813 | 126.0315 | C6H6O3 | 167.01 (11.4), 182.02 (22.4), 183 (100), 244.05 (10.8), 247.05 (10.2) | (Z). Tamarindienal? |
| 50 | 11.12 | 345.0843 | 166.0627 | C9H10O3 | 182.02 (100), 185.04 (26.4) | Ethylvanillin |
| 51 | 11.29 | 447.0656 | 88.0159 | C3H4O3 | 182.02 (100) | Reductone |
| 52 | 11.41 | 503.0923 | 144.0420 | C6H8O4 | 182.02 (100) | unknown |
| 53 | 11.56 | 329.0536 | 150.0315 | C8H6O3 | 65.01 (30.9), 66 (46.2), 66.01 (12.9), 76.02 (100), 78.96 (52.6), 82.04 (12), 83.02 (17.4), 89.01 (12), 91.02 (34.5), 96.97 (38.4), 99.08 (14.2), 99.92 (26.6), 105.02 (23.5), 106.04 (40.7), 108.02 (13), 109.03 (39.3), 116.93 (32.4), 118.03 (12.7), 120.01 (50.1), 121.03 (14.6), 122.02 (44.1), 127.11 (13.1), 129.09 (15), 135.02 (25.5), 151.01 (17.5), 152.02 (13.6), 163.03 (96.1), 164.01 (16.5), 165.02 (20.2), 169.02 (16), 171.1 (10.3), 181.01 (95.9), | 1,4-Benzodioxin-2(3H)-one |

TABLE 1-continued

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| | | | | | 182.02 (60.1), 199.13 (31.1), 201.11 (29.1), 224.06 (17.4), 253.05 (22.9), 254.06 (17.8), 328.18 (12.1), 329.23 (30.4) | |
| 54 | 11.62 | 253.0220 | 74.0003 | C2H2O3 | 65.01 (33.3), 66 (20.5), 66.01 (10.2), 76.02 (12.9), 78.96 (100), 91.03 (11.8), 96.96 (24.9), 96.97 (22.6), 106.04 (18.1), 120.01 (15.5), 122.02 (38.2), 125.04 (21.6), 135.02 (24.2), 138.02 (10.8), 152.02 (10.3), 156.06 (10.9), 164.01 (11.4), 181.01 (26.4), 182.02 (40.2), 183 (21.5), 235.08 (11.1) | Glyoxylic acid |
| 55 | 11.66 | 251.0788 | 72.0573 | C4H8O | 65.01 (25.9), 66 (14.6), 76.02 (28.6), 78.96 (13.2), 106.04 (35.1), 120.01 (13.6), 122.02 (100), 135.02 (13.3), 152.02 (49.4) | Butyraldehyde |
| 56 | 11.77 | 417.0564 | 58.0054 | C2H2O2 | 182.02 (100), 122.0236 (8.3), 76.0179 (3.1) | Glyoxal |
| 57 | 11.80 | 501.0777 | 142.0264 | C6H6O4 | 182.02 (100), 167.0090 (9.1), 122.0236 (2.8) | Dicarbonyls |
| 58 | 11.85 | 315.0741 | 136.0522 | C8H8O2 | 66 (13.1), 76.02 (35), 78.96 (50.6), 96.97 (100), 105.02 (10.4), 118.03 (15.5), 120.01 (19.1), 121.03 (33.2), 122.02 (20.4), 135.02 (13), 163.03 (25.7), 181.01 (30.1), 182.02 (20.2), 196.89 (21.9), 253.05 (39.3), 300.05 (10.1) | p-Methoxybenz-aldehyde |
| 59 | 11.87 | 285.0633 | 106.0417 | C7H6O | 50 (21.4), 65.01 (20.6), 66 (38.4), 76.02 (100), 78.96 (51.5), 82.04 (10.9), 96.97 (14.1), 105.02 (23.3), 106.04 (15.9), 118.03 (14.4), 120.01 (47.5), 121.03 (11.2), 122.02 (48.6), 125.01 (11.4), 135.02 (43.1), 151.01 (29.2), 163.03 (45.3), 164.01 (24.2), 166.04 (22.6), 169.02 (10.5), 181.01 (65.5), 182.02 (35.7), 186.87 (10.7), 208.06 (31.4), 238.06 (11.8) | Benzaldehyde |
| 60 | 12.07 | 475.0984 | 116.0471 | C5H8O3 | 182.02 (1.7), 122.0235 (100), 163.0252 (3.2), 122.02 (20.5), 138.02 | Ethyl pyruvate |
| 61 | 12.40 | 387.1688 | 208.1458 | C13H20O2 | (17.8), 152.02 (100), 168.02 (10.6), 272.1 (12.1), 342.15 (55.4), 343.15 (10.7) | Theaspirone A |
| 62 | 12.44 | 431.0717 | 72.0210 | C3H4O2 | 182.02 152.0218 (3.5), 122.0236 (3.1) | malondialdehyde |
| 63 | 12.49 | 331.0507 | 152.0318 | C4H8O6 | 65.01 (45.2), 66 (29), 66.01 (33.7), 76.02 (60.4), 78.96 (63), 82.04 (18.7), 83.02 (16.4), 89.01 (11.1), 90.01 (10.1), 91.03 (10.9), 92.02 (13.5), 92.93 (20.8), 94.92 (11.6), 96.97 (51.1), 99.92 (15.2), 105.02 (13.8), 106.04 (100), 107.03 (13.9), 109.01 (11.2), 116.93 (23.2), 118.04 (13.4), 120.01 (26.2), 120.06 (11.5), 121.05 (12.1), 122.02 (32.6), 123.03 (16.3), 124 (10.7), 130.04 (19.1), 131.04 (10.2), 132.06 (12.3), 135.02 | unknown |

TABLE 1-continued

Identification results of aldehydes and ketones based on UHPLC-Q-Orbitrap-MS/MS

| No. | $t_R$(min) | [M − H]⁻ | AKMass | AKFormula | MS/MS | Identification |
|---|---|---|---|---|---|---|
| | | | | | (15.2), 137.01 (31.2), 145.05 (12.3), 152.02 (11.2), 157.05 (13.5), 158.92 (12), 160.84 (17.4), 163.03 (47.1), 167.02 (23.5), 171.07 (10.6), 181.01 (38.2), 182.02 (27.8), 196.06 (10.2), 269.03 (67.3) | |
| 64 | 12.75 | 277.0940 | 98.0729 | C6H10O | 106.0399 (100), 65.0132 (69.4), 122.0236 (67.2), 181.0121 (42.7), 182.0205 (18.9), 76.0179 (40.2) | cyclohexanone |
| 65 | 12.90 | 683.1214 | 324.0719 | C13H8N8O3 | 167.03 (12.7), 179.02 (13.1), 182.02 (100), 197.03 (18.4) | Tricarbonyl |
| 66 | 13.04 | 279.1099 | 100.0885 | C6H12O | 106.0938 (100), 65.0132 (50.1), 122.0236 (26.7), 148.0619 (31.4) | Hexanal |
| 67 | 13.12 | 445.0878 | 86.0366 | C4H6O2 | 182.02 (100) | Butyraldehyde |
| 68 | 13.14 | 313.0944 | 134.0729 | C9H10O | 50 (13.3), 65.01 (14.2), 66 (23.7), 76.02 (82.1), 78.96 (32.7), 82.04 (10.7), 96.97 (43.9), 105.02 (17.9), 106.04 (11.5), 120.01 (35.7), 122.02 (33.1), 135.02 (35.7), 151.01 (36.2), 163.03 (47), 164.01 (24.5), 169.02 (10.9), 181.01 (100), 182.02 (37.2), 183.01 (20.9), 184.01 (23.9), 185.01 (13.4), 236.1 (22.2), 266.09 (15.3), 312.17 (33.7) | 4-methylacetophenone |
| 69 | 13.60 | 459.1025 | 100.0522 | C5H8O2 | 182.02 (100) | glutaraldehyde |
| 70 | 14.32 | 405.1780 | 226.1563 | C13H22O3 | 122.02 (12.6), 152.02 (100) | Methyl dihydrojasmonate |

The embodiments are preferred embodiments of the present invention and are not intended to limit the present invention. For those skilled in the art, the present invention may have various modifications and changes. Any modifications, equivalent substitutions, improvements, etc. made within the spirit and principles of the present invention shall be included in the protection scope of the present invention.

What is claimed is:

1. A non-targeted mass spectrometry identification method for identifying tobacco carbonyl components, comprising:
   soaking a tobacco product with water;
   oscillation extracting a tobacco extract from the tobacco product with acetonitrile;
   adding 2,4-dinitrophenylhydrazine (DNPH) to a first sample of the tobacco extract and derivatizing the first sample of the tobacco extract with the DNPH to obtain a first derivatized tobacco sample;
   adding DNPH-d₃ to a second sample of the tobacco extract and derivatizing the second sample of the tobacco extract with the DNPH-d₃ to obtain a second derivatized tobacco sample with an isotope-label;
   mixing the first derivatized tobacco sample and the second derivatized tobacco sample in a ratio of 1:1 thoroughly, and filtering the first and second derivatized tobacco samples through a filter membrane to obtain a third derivatized tobacco sample;
   preparing a blank sample by oscillation extracting a water extract from water with acetonitrile, derivatizing a first sample of the water extract with DNPH to obtain a first derivatized water sample, derivatizing a second sample of the water extract with DNPH-d₃ to obtain a second derivatized water sample, mixing the first derivatized water sample and the second derivatized water sample in a ratio of 1:1 thoroughly, and filtering the first and second derivatized water samples through a filter membrane to obtain the blank sample;
   performing ultra performance liquid chromatography (UPLC) and ion trap high resolution mass spectrometry (HRMS) on the first derivatized tobacco sample, the second derivatized tobacco sample, the third derivatized tobacco sample and the blank sample to obtain original LC-MS data;
   performing peak detection, peak alignment and peak grouping on the original LC-MS data to obtain original mass spectral feature data of coexisting target components and interfering components, including m/z values, retention times and peak intensities of chromatographic peaks;
   filtering the original mass spectral feature data based on statistical characteristics, mass loss, paired chromatographic peaks based on DNPH and DNPH-d₃ derivatization markers, and either secondary mass spectrometry or secondary mass spectrometry multiple ion mass spectrum characteristics to obtain final retained chromatographic peaks; and
   annotating the final retained chromatographic peaks and structurally identifying the tobacco carbonyl components using the final retained chromatographic peaks.

2. The method according to claim 1, wherein filtering the original mass spectral feature data based on statistical characteristics includes:

calculating the coefficient of variation (CV) and fold change (FC) according to the formulas CV=IntSQC/IntMQC$_1$×100%, where IntSQC represents a standard deviation of the peak intensity of a first one of the chromatographic peaks in the original LC-MS data for the first tobacco sample, and IntMQC$_1$ represents an average peak intensity, and FC=IntMQC$_2$/IntMBK, where IntMQC$_2$ represents an average peak intensity of the chromatographic peaks in the original LC-MS data for the first tobacco sample, and IntMBK represents an average peak intensity of the chromatographic peaks in the blank sample.

3. The method according to claim 1, wherein filtering the original mass spectral feature data based on the mass loss includes:

calculating according to the formula MD=|MZ−ceiling (MZ)|, wherein MZ represents an accurate mass of a precursor ion of a second one of the chromatographic peaks in the original LC-MS data for the first tobacco sample, and ceiling (MZ) is a ceiling number of the accurate mass.

4. The method according to claim 1, wherein filtering the original mass spectral feature data of the paired chromatographic peaks based on one or more DNPH and DNPH-d$_3$ derivatization markers includes: detecting a pair of chromatographic peaks of the third tobacco sample at a same retention time, then retaining the pair of chromatographic peaks when |MZ−MZd$_3$|=3.0186, |IntP1−IntP2|/max(P1, P2)<30%, and |RT1−RT2|<2, wherein MZ and MZd$_3$ respectively represent an accurate mass of a precursor ion in the first tobacco sample and an accurate mass of a precursor ion of an isotope d$_3$-labeled derivatization product in the second tobacco sample, IntP1 and IntP2 represent peak areas of first and second chromatographic peaks, respectively, and RT1 and RT2 represent retention times of the first and second chromatographic peaks, respectively.

5. The method according to claim 1, wherein the original mass spectral feature data are filtered based on secondary mass spectrometry multiple ion mass spectrum characteristics.

6. The method according to claim 1, wherein annotating or structurally identifying the final retained chromatographic peaks includes standard product matching, database searching, or cracking pattern analysis.

7. The method according to claim 1, wherein the ion trap HRMS comprises Orbitrap high resolution mass spectrometry.

8. The method according to claim 5, wherein filtering based on the secondary mass spectrometry multiple ion mass spectrum characteristics includes: when the secondary mass spectrum of the first tobacco sample produces fragment ions of m/z 76.018, m/z 120.008, m/z 122.024, m/z 135.019 and m/z 181.012, retaining the chromatographic peaks corresponding to the fragment ions.

9. The method according to claim 1, wherein filtering the original mass spectral feature data removes the original mass spectral feature data of the interfering components.

10. The method according to claim 9, wherein filtering the original mass spectral feature data further removes noise from the original mass spectral feature data.

11. The method according to claim 1, wherein the tobacco product comprises cut raw tobacco material, and the cut raw tobacco material is soaked in 5 mL of water for each 1 g of the cut raw tobacco material.

12. The method according to claim 1, wherein soaking the tobacco product with water comprises completely infiltrating the tobacco product with the water.

13. The method according to claim 1, wherein the tobacco product is oscillation extracted with 30 mL of the acetonitrile for each 1 g of the tobacco product, and the tobacco extract comprises the tobacco carbonyl components.

14. The method according to claim 1, wherein:

derivatizing the first sample of the tobacco extract with the DNPH comprises diluting the first sample of the tobacco extract and DNPH with acetonitrile to form a first derivatization reaction, shaking the first derivatization reaction, and keeping the first derivatization reaction at room temperature for 30 minutes; and derivatizing the second sample of the tobacco extract with the DNPH-d$_3$ comprises diluting the second sample of the tobacco extract and DNPH-d$_3$ with acetonitrile to form a second derivatization reaction, shaking the second derivatization reaction, and keeping the second derivatization reaction at room temperature for 30 minutes.

15. The method according to claim 1, wherein the first and second derivatized tobacco samples are filtered through a 0.22 μm organic phase filter.

16. The method according to claim 1, wherein the UPLC and the HRMS are performed with an instrument platform comprising an UHPLC system and a mass spectrometer, connected in series.

17. The method according to claim 16, wherein the HRMS is performed using conditions including a spray voltage of 3.7 kV, a sheath gas flow rate of 35 L/min, an auxiliary gas flow rate of 10 L/min, and a transfer tube temperature of 350° C.

18. The method according to claim 1, wherein the HRMS is performed using conditions further including a mass-to-charge ratio scanning range set to 100-1200 m/z, a resolution of 70,000, a mass-to-charge ratio scanning resolution of 35,000, and a high-energy collision-induced dissociation voltage of 30 eV.

19. The method according to claim 2, wherein filtering the original mass spectral feature data based on the statistical characteristics further comprises retaining the first one of the chromatographic peaks when CV≤30% and FC≥1.5.

20. The method according to claim 3, wherein filtering the original mass spectral feature data based on the mass loss further comprises retaining the second one of the chromatographic peaks when 0.02≤MD≤0.3 and m/z>209.

* * * * *